(12) United States Patent
Burkinshaw et al.

(10) Patent No.: US 6,183,516 B1
(45) Date of Patent: Feb. 6, 2001

US006183516B1

(54) METHOD FOR IMPROVED BONDING OF PROSTHETIC DEVICES TO BONE

(75) Inventors: Brian D. Burkinshaw, Pflugerville; Jack R. Frautschi, Athens, both of TX (US)

(73) Assignee: Sulzer Orthopedics Inc., Austin, TX (US)

( * ) Notice: Under 35 U.S.C. 154(b), the term of this patent shall be extended for 0 days.

(21) Appl. No.: 09/168,798

(22) Filed: Oct. 8, 1998

(51) Int. Cl.⁷ .................................................. A61F 2/28
(52) U.S. Cl. .................................... 623/16.11; 623/23.62
(58) Field of Search .................... 623/16.11, 23.56, 623/23.57, 23.62, 76, 92; 427/2.1, 2.12, 2.24, 2.26

(56) References Cited

U.S. PATENT DOCUMENTS

| | | | |
|---|---|---|---|
| 4,202,055 | * 5/1980 | Reiner et al. | 623/23 |
| 4,365,359 | * 12/1982 | Raab | 623/16 |
| 5,258,041 | * 11/1993 | Guire et al. | 623/66 |
| 5,344,701 | * 9/1994 | Gagnon et al. | 428/304.4 |
| 5,538,514 | * 7/1996 | Hawkins | 623/16 |
| 5,563,056 | * 10/1996 | Swan et al. | 435/180 |
| 5,997,517 | * 12/1999 | Whitbourne | 604/265 |

OTHER PUBLICATIONS

Spire Corporation; Surface Treatment Process for Enhanced Cement Adhesion to UHMWPE; Jan. 1, 1995.

* cited by examiner

*Primary Examiner*—David J. Isabella
(74) *Attorney, Agent, or Firm*—Philip S. Lyren

(57) ABSTRACT

The surface molecules of a modified polymeric prosthetic device participate in the free radical polymerization reaction of a bone cement such as polymethylmethacrylate, thereby providing improved bonding between the prosthesis and the bone to which it is attached.

13 Claims, No Drawings

METHOD FOR IMPROVED BONDING OF PROSTHETIC DEVICES TO BONE

BACKGROUND OF THE INVENTION

The present invention relates generally to methods for chemically bonding two dissimilar polymers. More particularly, it is directed to a method for providing covalent bonding between a polymeric prosthetic device and polymethylmethacrylate bone cement.

Numerous surgical procedures are available for the reconstruction and/or repair of bones. Many such methods involve the use of prosthetic devices produced from polymeric materials such as polyethylene. Indeed, a variety of polymeric prostheses are commercially available for use in repairing damaged hip joints, knee joints etc., due to such diseases as osteoarthritis, rheumatoid arthritis, traumatic arthritis, avascular necrosis, sickle cell anemia and osteoporosis.

The most common technique for reconstructing damaged bone tissue involves initially cutting and drilling the bone so that it conforms to the shape of the securement portion of a prosthesis. A number of shallow holes are generally drilled or cut into the surfaces of the bone tissue adjacent to the prosthesis in order to form projecting cavities into which bone cement can flow so as to form a strong mechanical interlock between the cement and the bone tissue.

In the majority of such procedures, the prosthesis is secured into place by use of polymethylmethacrylate (PMMA) bone cement. PMMA is a self-curing acrylic resin; it polymerizes at room temperature without any external application of heat. However, PMMA is a "luting" agent, rather than an adhesive, i.e., the cement does not produce any chemical bond with bone tissue to hold the prosthesis in place. Rather, the PMMA fills irregularities in the bone and hardens to form a mechanical interlock. Because the bond so formed is mechanical in nature, preparation and application technique can be very important in the overall success of these procedures. Ineffective bond formation can result in eventual loosening of the prosthesis and failure of the product. This, in turn, results in discomfort to the patient and a need for surgical replacement of the prosthesis.

U.S. Pat. Nos. 5,002,582 and 5,512,329 report methods for the preparation of modified surfaces by covalently bonding polymer molecules thereto by external activation of latent reactive groups, such as photactivatable ketones, carried by the polymer molecules. The polymer molecules are so spatially oriented as to enable one or more of the latent reactive groups to come into covalent bonding proximity with the substrate surface. Upon activation of the latent reactive groups by applying external stimulation, typically ultraviolet radiation, covalent bonds can be formed between the latent reactive group and the substrate.

There is a need in the orthopedic arts for simple and cost effective methods for providing improved adhesion between a prosthetic device and the bone cement to which it is bonded. A great deal of effort and expense has been directed at attempts to provide such improved attachment methods. However, for the most part, these attempts have proved largely unsuccessful and most surgeons continue to utilize PMMA in the manner described above. We provide herein a method for producing prostheses that are attached to bone cement via covalent chemical bonding, resulting in improved bonding strength between a polymeric prosthetic device and bone.

SUMMARY OF THE INVENTION

In a first aspect of this invention there is provided a method for achieving improved bonding between a polymeric prosthetic device and bone. The method involves producing a surface modified prosthetic device by reacting the surface of a prosthetic device with one or more of the disclosed surface modifying agents. A surface modifying agent of the invention comprises a first reactive group and a second reactive group. When a surface modifying agent is reacted under appropriate conditions with the surface of a prosthetic device, the first reactive group becomes covalently bonded to a plurality of the surface molecules of the prosthetic device.

Therefore, in another aspect of the invention there is provided a surface modified polymeric prosthetic device that is capable of improved bonding with a bone cement such as PMMA. The surface molecules of the surface modified prosthetic device are covalently bonded to the surface modifying agent via the first reactive group, whereas the second reactive group is available for participation in the polymerization reaction of the bone cement.

In another aspect of the invention, the surface modified prosthetic device is contacted with bone in the presence of a bone cement such as PMMA under conditions effective to cause covalent bonding between the second reactive group on the surface modified prosthetic device and the PMMA. As a result, a surface modified prosthetic device of the invention can be attached to bone with improved adhesive strength by virtue of the covalent bond formed between the surface of the modified device and the bone cement with which it is contacted.

DETAILED DESCRIPTION OF INVENTION

Prior to the present invention, the adhesion of prosthetic devices to bone surfaces has for the most part been mechanical in nature. In a typical procedure, the surface of the device is roughened or otherwise prepared before bone cement is applied so as to increase the resulting degree of mechanical adhesion. However, mechanical adhesion can be problematic and failure of the bond between a prosthesis and bone is not uncommon. It would be preferred for such prostheses to be directly or indirectly chemically bonded to the surfaces to which they are applied, for example by creating a permanent chemical bond between the bone cement and the surface of the prosthesis.

Therefore, in accordance with one aspect of the present invention, there is provided a method for improved bonding between a prosthetic device and bone cement, and as a result between the prosthetic device and bone. The surface of the prosthetic device is modified by reaction with a compound referred to herein as a surface modifying agent. The surface modifying agent contains at least one chemical group/functionality that is reactive with the polymeric surface of the prosthetic device, hereinafter referred to as the first reactive group. The surface modifying agent also contains at least one chemical group/functionality that is reactive with bone cement, said group being hereinafter referred to as the second reactive group.

Thus, the surface modifying agents of the present invention are bifunctional, i.e., they contain functionalities that are reactive both with the polymer surface of a prosthetic device and with monomer, oligomer and/or polymer of the bone cement being used. As a result, prostheses can be bonded to bone with improved adhesion strength by virtue of the covalent bond formed between the surface molecules of the prosthesis and bone cement.

The first reactive group of the surface modifying agent of the invention can be broadly defined as a group which can respond to a specific applied external stimulus to undergo active specie generation, where the active species so produced is capable of becoming chemically bonded to the surface of a polymeric prosthetic device. Thus, the first reactive group is the atom or group of atoms on the surface modifying agent which retains its chemical structure substantially unchanged under conditions of storage but which, upon activation, is capable of forming one or more covalent bonds with the polymer molecules on the surface of the prosthetic device.

The first reactive group of the surface modifying agent may be chosen to be responsive to various portions of the electromagnetic spectrum; those that are responsive to ultraviolet, visible or infrared portions of the spectrum are typically preferred. Such reactive groups have been referred to as latent reactive groups and are generally well known, as are the residues formed upon activation and reaction with a substrate (see for example U.S. Pat. No. 5,002,582, incorporated herein by reference). Upon application of the appropriate external stimulus, the first reactive group generates active species such as free radicals, nitrenes, carbenes, and excited states of ketones, which can react with the surface of the prosthetic device.

The azides constitute one preferred class from which the first reactive group can be selected. These can include, for example, arylazides:

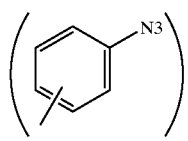

such as phenyl azide and particularly 4-fluoro-3-nitrophenyl azide;

acyl azides:

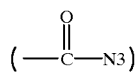

such as benzoyl azide and p-methylbenzoyl azide;

azido formates:

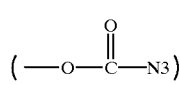

such as ethyl azidoformate and phenyl azidoformate;

sulfonyl azides

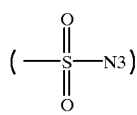

such as benzenesulfonyl azide; and phosphoryl azides

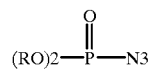

such as diphenyl phosphoryl azide and diethyl phosphoryl azide.

Diazo compounds constitute another preferred class from which a first reactive group can be selected. These can include, for example, diazoalkanes (—$CHN_2$) such as diazomethane and diphenyldiazomethane, diazoketones:

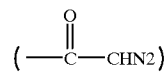

such as diazoacetophenone and 1-trifluoromethyl-1-diazo-2-pentanone;

diazoacetates:

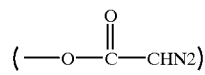

such as t-butyl diazoacetate and phenyl diazoacetates;

beta-ketone-alpha-diazoacetates:

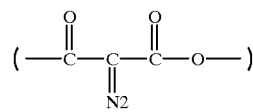

such as t butyl alpha diazoacetoacetate, etc.

Other first reactive groups suitable for use in the surface modifying agents of the invention include the aliphatic azo compounds such as azobisisobutyronitrile, the diazirines such as 3-trifluoromethyl-3-phenyldiazirine, the ketenes (—CH=C=O) such as ketene and diphenylketene and photoactivatable ketones such as benzophenone and acetophenone. Peroxy compounds are contemplated as another class of first reactive groups and include dialkyl peroxides such as di-t-butyl peroxide and dicyclohexyl peroxide, diacyl peroxides such as dibenzoyl peroxide and diacetyl peroxide, and peroxyesters such as ethyl peroxybenzoate.

The second reactive group of the surface modifying agent of the invention represents a chemical group/functionality that is capable under appropriate conditions of covalent bonding to monomers, oligomers and/or polymers of a suitable bone cement. The bone cement can be essentially any polymeric cementing compound that is compatible with bone and that is capable of participating in a free radical polymerization reaction. These can include PMMA, polyvinylidine chloride, polyisobutylene etc. PMMA is the preferred bone cement for use in this invention based on its widespread acceptance and use among orthopedic practitioners.

One preferred second reactive group that is reactive with monomers, oligomers and/or polymers of PMMA is a vinyl group. It should be noted, however, that essentially any other chemical group/functionality is also suitable provided it is capable of participating in the free radical polymerization reaction of PMMA.

In practice it would be typical to first modify the surface of the polymeric prosthetic device by reaction with a surface modifying agent of the invention via the first reactive group. The conditions for this type of reaction are known and can be readily optimized by the skilled individual, particularly in view of disclosures such as U.S. Pat. No. 5,002,582.

Therefore, in another aspect of this invention there is provided a surface modified prosthetic device that has been reacted with a surface modifying agent of the invention so that said agent is covalently linked to the surface of the device via its first reactive groups. This surface modified prosthetic device contains unreacted second reactive groups that are available for participation in the free radical polymerization reaction of a bone cement such as PMMA. As a result, the second reactive group, and therefore the surface of the modified prosthesis, becomes covalently bonded within the bone cement during cement polymerization.

The loading density resulting from attachment of surface modifying agent to a polymeric prosthetic device in accordance with the invention may be regulated in several ways. First, the degree of activation of first reactive groups is generally a function of the quantity of the external stimulus that is applied, and thus the extent of covalent bonding through the first reactive groups may be regulated by regulating the intensity and time of application of the applied stimulus. Regulation of the applied stimulus is particularly easy when the stimulus is actinic radiation; one can readily regulate the amount of radiation to which the first reactive groups are exposed. Loading density may also be regulated by adjusting the capacity of first reactive groups to come into bonding proximity with the polymeric surface. Thus, one may regulate the viscosity of a solution in an appropriate solvent as well as the solubility of polymer in the solvent. Yet another factor is the concentration of molecules containing the first reactive groups in a composition to be used to modify the surface.

The surface modified prosthesis so produced, bearing a surface modifying agent on its surface attached via the first reactive group, can be used in a typical orthopedic procedure using conventional bone cements such as PMMA. This generally involves a room temperature polymerization reaction initiated by the presence of a free-radical-generating catalyst, such as a peroxide. The precise conditions for the reaction are not critical and those known in the art are generally suitable.

As will be understood from the above discussion and from the examples which follow, the invention permits a substrate, particularly a polymeric prosthesis surface, to be provided with covalently attached molecules in sufficient loading density and/or quantity as to provide a surface having the physical properties necessary to become chemically bonded to PMMA or another bone cement during free radical polymerization of the cement.

Any prosthetic device type bonded to bone using a bone cement can be used with the present invention. Exemplary prosthetic device types include, but are not limited to, hip joints and knee joints, among others.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Ultra-High Molecular Weight Polyethylene (UHMWPE) disks were attached to pull-tabs with polymethylmethacrylate (PMMA) and then destructively tested under tensile conditions. The purpose of the test was to quantify the improvement in bonding strength of PMMA to UHMWPE following surface modification of the disks. Four groups were tested: control (untreated), and those subjected to either Treatment A, B or C, as further described below.

Treatment A used polyacrylamide as the surface modifying agent. The disks were wet coated and then gamma sterilized. Treatments B and C both used polyvinylpyrrilodine (PVP) as the surface modifying agent. The PVP was dry coated onto the disks and then ultraviolet cured. The techniques used were as described by Guire et al., U.S. Pat. No. 5,002,582, incorporated herein by reference.

Once the disks were surface modified, the disks were attached to the pull-tabs using PMMA at room temperature and sufficient time was allowed for the PMMA to fully set. PMMA mantle thickness was 0.12 inches; PMMA/UHMWPE contact area was 0.75–1.0 square inches.

Test conditions were as follows: tensile load rate was 0.05 inches/min on an Instron 4204 Universal Testing Machine, and pure uniaxial tension was achieved via universal tensile fixtures.

The following results were obtained:

| Treatment | Load to Failure (lb) | Mean |
|---|---|---|
| Control | 2.7 | |
| | 5.9 | |
| | 6.1 | |
| | 3.2 | |
| | 4.3 | |
| | | 4.4±1.5 |
| Treatment A | 24.4 | |
| | 26.6 | |
| | 6.7 | |
| | 27.1 | |
| | 8.6 | |
| | | 18.7±10.1 |
| Treatment B | 29.5 | |
| | 70.3 | |
| | 11.0 | |
| | 38.7 | |
| | 42.4 | |
| | | 38.4±21.6 |
| Treatment C | 164.4 | |
| | 41.6 | |
| | 0.3 | |
| | 72.0 | |
| | 7.1 | |
| | | 57.1±66.5 |

Thus, the mean tensile bonding strength of the treatment groups was significantly higher than untreated controls. Compared with the control samples, there was a 425% increase in mean tensile bonding strength for treatment group A, a 872% increase for group B, and a 1298% increase for group C.

All of compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for providing improved bonding between a polymeric prosthetic device and bone comprising:

producing a surface modified prosthetic device by reacting the surface of a prosthetic device with a surface modifying agent which comprises a first reactive group and a second reactive group under conditions effective to cause covalent bonding between the first reactive group and the surface molecules of the polymeric prosthetic device; and contacting the surface modified prosthetic device with bone in the presence of PMMA under conditions effective to cause covalent bonding between the second reactive group on the surface modified prosthetic device and the PMMA, wherein the second reactive group is capable of participating in the polymerization reaction of PMMA.

2. The method of claim 1, wherein the first reactive group is derived from an azide, diazo, aliphatic azo, diazirine, ketene, ketone, or peroxy compound.

3. The method of claim 1, wherein the first reactive group is derived from an azide compound selected from the group consisting of aryl azides, acyl azides, azido formates, sulfonyl azides, and phosphoryl azides.

4. The method of claim 1, wherein the first reactive group is derived from a diazo compound selected from the group consisting of diazoalkanes, diazoketones, and diazoacetates.

5. The method of claim 1, wherein the second reactive group is a vinyl group.

6. The method of claim 1, wherein the polymeric prosthetic device is made from polyethylene.

7. A surface modified polymeric prosthetic device capable of improved bonding to PMMA wherein surface molecules of the prosthetic device are covalently bonded to the first reactive group of a surface modifying agent which comprises a first reactive group and a second reactive group, wherein the second reactive group is capable of participating in the polymerization reaction of PMMA.

8. The surface modified polymeric prosthetic device of claim 7, wherein the first reactive group is derived from an azide, diazo, aliphatic azo, diazirine, ketene, ketone, or peroxy compound.

9. The surface modified polymeric prosthetic device of claim 7, wherein the first reactive group is derived from an azide compound selected from the group consisting of aryl azides, acyl azides, azido formates, sulfonyl azides, and phosphoryl azides.

10. The surface modified polymeric prosthetic device of claim 7, wherein the first reactive group is derived from a diazo compound selected from the group consisting of diazoalkanes, diazoketones, and diazoacetates.

11. The surface modified polymeric prosthetic device of claim 7, wherein the second reactive group is a vinyl group.

12. The surface modified polymeric prosthetic device of claim 7, wherein the polymeric prosthetic device is made from polyethylene.

13. A method for providing improved bonding between a polymeric prosthetic device and bone comprising:

producing a surface modified prosthetic device by reacting the surface of a prosthetic device with a surface modifying agent which comprises a first reactive group selected from the group consisting of azide, diazo, aliphatic azo, diazirine, ketene, ketone, and peroxy groups, and a second reactive group under conditions effective to cause covalent bonding between the first reactive group and the surface molecules of the polymeric prosthetic device; and contacting the surface modified prosthetic device with bone in the presence of PMMA under conditions effective to cause covalent bonding between the second reactive group on the surface modified prosthetic device and the PMMA.

* * * * *